US009339772B1

United States Patent
Brav et al.

(10) Patent No.: US 9,339,772 B1
(45) Date of Patent: May 17, 2016

(54) USING VORTEX RINGS TO DELIVER GASES AT A DISTANCE

(71) Applicant: Elwha LLC, Bellevue, WA (US)

(72) Inventors: Ehren J. Brav, Bainbridge Island, WA (US); William D. Duncan, Mill Creek, WA (US); Roderick A. Hyde, Redmond, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 0 days.

(21) Appl. No.: 14/681,962

(22) Filed: Apr. 8, 2015

Related U.S. Application Data

(63) Continuation of application No. 14/562,262, filed on Dec. 5, 2014.

(51) Int. Cl.
*B01F 3/04* (2006.01)
(52) U.S. Cl.
CPC ......... *B01F 3/04014* (2013.01); *B01F 3/04049* (2013.01)
(58) Field of Classification Search
CPC .... B01F 3/04; B01F 3/04014; B01F 3/04049; G08B 6/00
USPC ...................... 261/26, 30, 76, 78.1
See application file for complete search history.

(56) References Cited

U.S. PATENT DOCUMENTS

| | | | |
|---|---|---|---|
| 5,690,165 A | 11/1997 | Roth et al. | |
| 6,357,726 B1 | 3/2002 | Watkins | |
| 6,536,746 B2 | 3/2003 | Watkins | |
| 6,786,474 B2 | 9/2004 | Watkins et al. | |
| 6,994,328 B2 | 2/2006 | Watkins et al. | |
| 7,059,544 B2 | 6/2006 | Leonard et al. | |
| 9,092,953 B1 * | 7/2015 | Mortimer | G08B 6/00 |
| 2002/0036358 A1 | 3/2002 | Watkins | |
| 2003/0173685 A1 | 9/2003 | Watkins et al. | |
| 2004/0195351 A1 | 10/2004 | Leonard et al. | |
| 2005/0046049 A1 | 3/2005 | Watkins et al. | |
| 2008/0290189 A1 | 11/2008 | Levi | |
| 2009/0108094 A1 | 4/2009 | Ivri | |

OTHER PUBLICATIONS

Smith et al., "Small-scale structure in colliding off-axis vortex rings", Journal of Fluid Mechanics, vol. 259, 1994, pp. 281-290.
Zelano et al., "Attentional modulation in human primary olfactory cortex." Nature Neuroscience, Jan. 2005, pp. 114-120.

* cited by examiner

*Primary Examiner* — Robert A Hopkins
(74) *Attorney, Agent, or Firm* — Foley & Lardner LLP

(57) ABSTRACT

A system for delivering vortex rings to an intended target includes a vortex ring generator, one or more component storage containers, and a component additive mechanism. The vortex ring generator is configured to deliver and air vortex rings. The component additive mechanism is configured to remove a component from at least one of the one or more component storage containers, generate a gas from the component, and to add the gas to a vortex ring after the vortex ring is generated by the vortex ring generator.

33 Claims, 4 Drawing Sheets

USING VORTEX RINGS TO DELIVER GASES AT A DISTANCE

CROSS-REFERENCE TO RELATED PATENT APPLICATIONS

This application is a continuation of U.S. patent application Ser. No. 14/562,262, filed Dec. 5, 2014, which is incorporated herein by reference in its entirety.

BACKGROUND

Gases may be delivered into a space for many purposes, such as enhancing the smell of a room, intensifying the taste of food, delivering medicine, and dispersing groups of people. Gases may be directly delivered to a person through tubes, pipes, or even through the air. Toroidal vortex rings may be used to deliver gases through another fluid (e.g., air or water) over large distances due to pressure differences in and around vortex rings which prevent the rings from immediately dissipating in the atmosphere. Vortex rings may be formed from many different gases to deliver various substances without the need for connecting structural components.

SUMMARY

One embodiment relates to a vortex ring delivery system. The vortex ring delivery system includes a vortex ring generator, one or more component storage containers, and a component additive mechanism. The vortex ring generator is configured to deliver and aim vortex rings. The component additive mechanism is configured to remove a component from at least one of the one or more component storage containers, generate a gas from the component, and to add the gas to a vortex ring after the vortex ring is generated by the vortex ring generator.

Another embodiment relates to a vortex ring delivery system that includes a vortex ring delivery module, a sensor, and a control module. The vortex ring delivery module includes a vortex ring generator, one or more component storage containers, and an aiming nozzle. The vortex ring delivery module is configured to deliver and aim vortex rings. The sensor is configured to acquire sensor data regarding the tracking of vortex rings and an intended target. The control module is configured to control operation of the vortex ring delivery module based on the sensor data.

Another embodiment relates to a vortex ring delivery system that includes a vortex ring generator, a sensor, and a control module. The vortex ring generator is configured to deliver and aim vortex rings. The sensor is configured to acquire sensor data regarding the trajectory of the vortex rings and an intended target. The control module is configured to control operation of the vortex ring generator based on the sensor data.

Another embodiment relates to a system for delivering directional smell cues that includes a vortex ring delivery module, a sensor, and a control module. The vortex ring delivery module is configured to generate, aim, and deliver vortex rings. The sensor is configured to acquire sensor data regarding the trajectory of the vortex rings, the location of an intended target, and the intended target's reaction to the vortex rings. The control module is configured to control operation of the vortex ring delivery module based on the sensor data. The control module is also configured to determine if the vortex rings reach the intended target and whether the vortex ring delivery module should generate, aim, and deliver additional vortex rings.

Another embodiment relates to a method for delivering vortex rings. The method includes receiving, by a control module, inputs regarding an intended target; combining one or more components to form a gas combination; generating vortex rings using a vortex ring generator; adding, by a component additive mechanism, the gas combination to the generated vortex rings; steering the generated vortex rings using an aiming nozzle; and monitoring the trajectory of the launched vortex rings and the intended target using a sensor.

Another embodiment relates to a method for delivering vortex rings. The method includes receiving inputs regarding an intended target using a control module; launching a first vortex ring toward the intended target using a vortex ring generator; incorporating a gas into the first vortex ring using a component additive mechanism; acquiring sensor data regarding the intended target using a sensor; and aiming and launching a second vortex ring at the intended target using the vortex ring generator based on the sensor data.

Another embodiment relates to a method for delivering directional smell cues. The method includes identifying an intended target; determining a desired reaction of the intended target; generating and delivering vortex rings to the intended target using a vortex ring generator and component additive mechanism; tracking the vortex rings and monitoring the intended target using a sensor; and selectively delivering additional vortex rings based on determining if the vortex ring reached the intended target and if the desired reaction was made by the intended target.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 is an illustration of a vortex ring delivery system according to one embodiment.

FIG. 2 is an illustration of a vortex ring forming upon launch by a vortex ring delivery system according to one embodiment.

FIG. 3 is an illustration of a network of vortex ring delivery systems according to one embodiment.

FIG. 4 is a diagram of a method for delivering vortex rings according to one embodiment.

FIG. 5 is a diagram of a method for delivering vortex rings according to another embodiment.

FIG. 6 is a diagram of a method for delivering directional smell cues according to one embodiment.

DETAILED DESCRIPTION

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring to the figures generally, systems and methods for delivering vortex rings are shown according to various embodiments. Vortex rings may be delivered across distances due to pressure differences in and around a vortex ring, which prevents the vortex ring from immediately dissipating in the surrounding environment. Upon slowing down or otherwise being obstructed, vortex rings break down and dissipate. Components may be incorporated into a vortex ring before, during, or after the formation of the vortex ring. Various aspects of the formation, behavior, and applications of vortex rings are described in U.S. Pat. Nos. 6,994,328, 6,786,474, 6,536,746, and 6,357,726, which are incorporated herein by reference. Vortex ring applications vary from simple air fresheners that propel a smell across a room to research efforts for high-powered military applications. At high enough velocities, a vortex ring (or a series of many vortex rings) traveling through air may concuss or knock unconscious living creatures. Vortex rings are not limited to carrying only smells and may also be used to deliver medicines, hormones, or other substances that may be carried through air without requiring permanent or temporary structures of tubes or gas piping.

Figure 1:
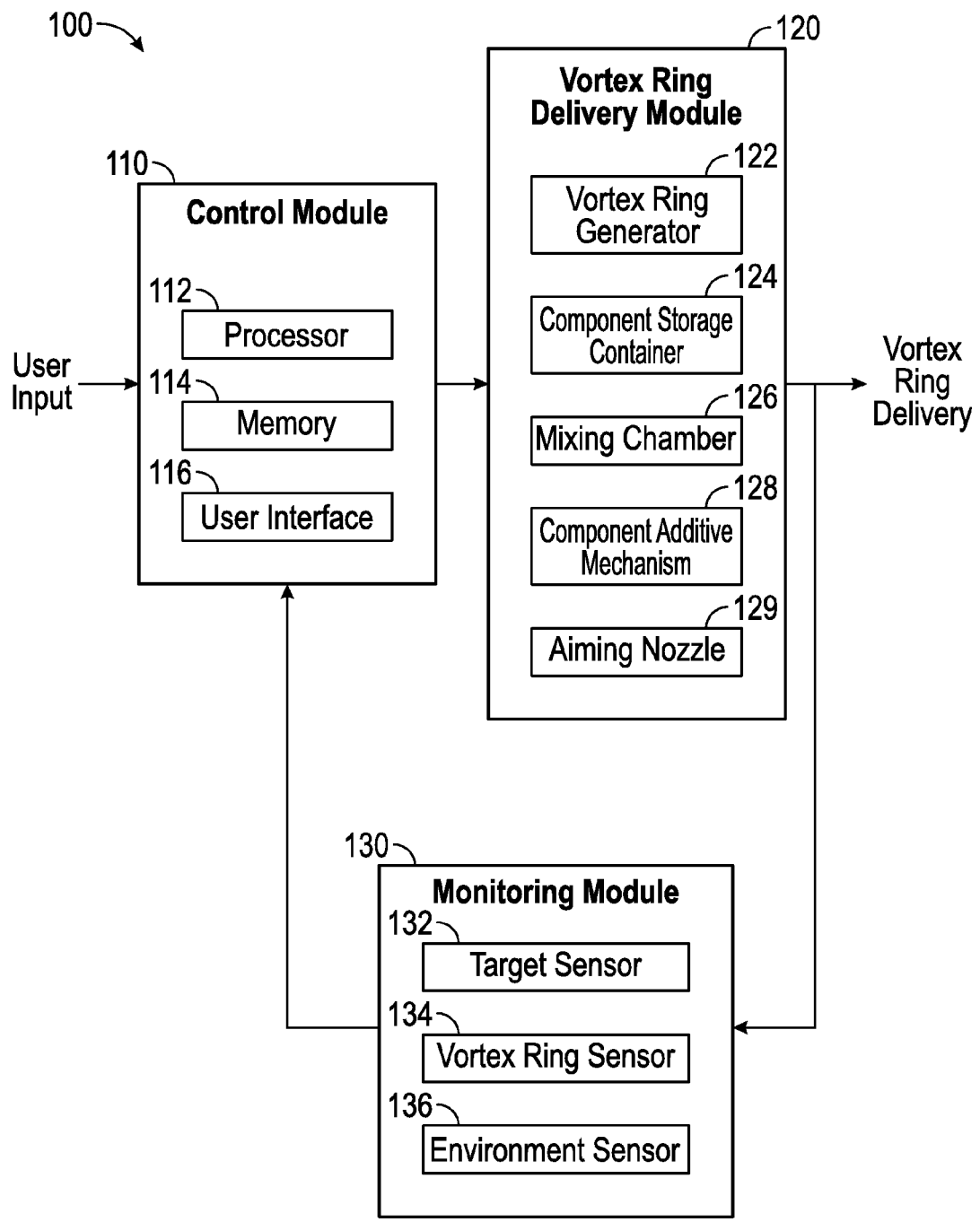

Referring now to FIG. 1, system 100 for delivering vortex rings is shown according to one embodiment. As shown in FIG. 1, system 100 includes control module 110, vortex ring delivery module 120 and monitoring system 130. Control module 110 may include processor 112, memory 114, and user interface 116. Control module 110 is configured to receive inputs, including control inputs and monitoring inputs. For example, control module 110 may receive a control input from a user to aim or launch vortex rings from vortex ring delivery module 120, or control module 110 may receive a monitoring input from monitoring system 130 to determine if a vortex ring successfully launched or reached an intended target. Control module 110 may receive user inputs through user interface 116 or from an input/output device, such as a computer, a mobile device, tablet, iPad, or the like. Control module 110 may generate and display results, success rates, usage statistics, and other information using user interface 116 or an input/output device. Control module 110 is configured to control vortex ring delivery module 120 by providing a system input. For example, the system input may cause vortex ring delivery module 120 to launch vortex rings at a certain target, to deliver a certain smell to an area, or to cause an intended target to make a certain reaction.

As shown in FIG. 1, control module 110 includes processor 112 and memory 114. Processor 112 may be implemented as a general-purpose processor, an application specific integrated circuit (ASIC), one or more field programmable gate arrays (FPGAs), a digital-signal-processor (DSP), a group of processing components, or other suitable electronic processing components. Memory 114 is one or more devices (e.g., RAM, ROM, Flash Memory, hard disk storage, etc.) for storing data and/or computer code for facilitating the various processes described herein. Memory 114 may be or include non-transient volatile memory or non-volatile memory. Memory 114 may include database components, object code components, script components, or any other type of information structure for supporting the various activities and information structures described herein. Memory 114 may be communicably connected to processor 112 and provide computer code or instructions to processor 112 for executing the processes described herein.

Figure 2:
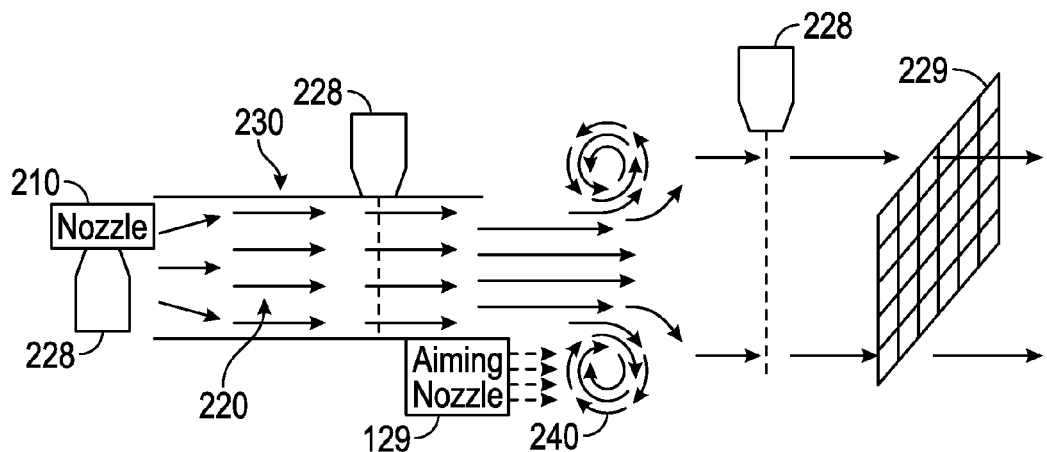

Vortex ring delivery module 120 is configured to launch vortex rings according to a system input provided by control module 110. Vortex ring delivery module 120 may include vortex ring generator 122, component storage container 124, mixing chamber 126, component additive mechanism 128, and aiming nozzle 129. Vortex ring generator 122 launches vortex rings in a desired direction. Vortex ring generator 122 may launch vortex rings using a nozzle, a vibratable diaphragm that pulses gas through an opening, or by otherwise forcing gas through an opening. In one embodiment, vortex ring generator 122 launches vortex rings by forcing gas through a hollow cylinder. Gas is forced through the cylinder using a nozzle, combustion, or controlled explosions. For example, referring to FIG. 2, nozzle 210 ejects gas 220 at a high pressure through hollow cylinder 230. Upon exiting hollow cylinder 230, gas 220 spills over the diameter of cylinder 230 forming vortex ring 240 that continues traveling in the launch direction. During formation, vortex ring 240 entrains ambient air, thereby resulting in a vortex ring including gas 220 and ambient air.

As used herein, the gaseous mass that is launched or monitored by system for delivering vortex rings 100 is commonly referred to as a "vortex ring" or "ring." However, many different configurations or shapes of gaseous masses may be launched or delivered through air. The terms "vortex ring" and "ring" are used for the sake of clarity and in no way should be read as limiting.

In any of the examples contained herein, whenever it is mentioned that a component is added to vortex ring 240, it is also contemplated that the component may be added to gas 220 before gas 220 forms vortex ring 240. In some embodiments, component additive mechanism 128 adds components to vortex ring 240 before vortex ring 240 reaches the intended target. Components may be added to vortex rings by spray, vaporization, ultrasonic vaporization, heat, evaporation, etc. In one embodiment, components are added to gas 220 before the gas forms vortex ring 240. For example, components are added to gas 220 before the gas exits hollow cylinder 230. In one embodiment, component additive mechanism 128 includes nozzle 228 to spray components into the areas where vortex ring 240 is formed such that vortex ring 240 entrains the components along with, or instead of, ambient air. Many types of substances may be added to vortex rings before the rings reach an intended target, including smellable components, smell-canceling components, medicinal components (e.g., oxytocin, testosterone), memory inducing components, taste enhancing components, fluorescent components, or hormonal components, among others. Components may be entrained by vortex rings after the rings have formed. For example, nozzle 228 may spray gaseous components between vortex ring generator 122 and the intended target such that vortex rings entrain the gaseous components while traveling toward the intended target. In one embodiment, vortex ring 240 passes through mesh 229 that contains components such that the components are entrained by vortex ring 240. The mesh may incorporate the components in a thermally releasable form (e.g., as a coating or constituent of the mesh released as the mesh is heated, for instance, resistively). In another embodiment, the component is in liquid form and wets the mesh, using surface tension forces to hold the liquid component on the mesh and to distribute the component along the mesh. Vortex ring delivery module 120 may cause vortex ring 240 to entrain components sprayed between vortex ring generator 122 and an intended target and components from mesh 229 such that a greater concentration of added components are carried to the intended target or for purposes of adding multiple types of components to vortex ring 240. In some cases, components are mixed in mixing chamber 126 before being added to vortex ring 240.

Vortex ring delivery module 120 includes component storage container 124 to store components before the components are added to vortex ring 240. Component storage container 124 may include a single container for storing components, or alternatively, component storage container 124 may include multiple containers for storing a single type of component or multiple types of components. The component may be stored as a liquid or as a solid before being added to vortex ring 240. The component, otherwise referred to as "added components," may include a wide-range of component types, including pheromones, adhesive components, time-delay components, release-on-event components, smellable components, fluorescent components, medicinal components, hormonal components, smell-cancelling components, and reactant components. For example, adhesive components may stick to the skin, clothing, or structure of an intended target such that the components cannot be easily removed. The adhesive components may be configured to only stick to certain surface types. For example, some components may only adhere to hair follicles or nylon fabric. Time-delay components may stick to an intended target and become activated after a certain period of time. For example, time-delay smellable components may adhere to hair follicles in a target's nostril and remain smell neutral until a certain time elapses (e.g., five minutes), thereafter providing a smell. Likewise, release-on-event components may become activated upon a certain event. For example, release-on-event smellable components may adhere to an intended target's clothing such that when the intended target walks outside (e.g., is exposed to fresh air, sunlight, a breeze, or a temperature difference) the release-on-event smellable components are activated, thereby providing a smell. The components may be encapsulated in different membranes, for example, micelles or liposomes. Added components may also be intended to react with other substances, for example, certain perfumes, body odors, or food smells. The components may increase the smell of other substances or reduce or completely cancel such smells. For example, the components may reduce or completely cancel smells using receptor antagonists or maskants.

In one embodiment, vortex ring delivery module 120 includes aiming nozzle 129 to aim or steer vortex rings such that vortex rings reach the intended target. Aiming nozzle 129 may be a single nozzle or may include multiple aiming nozzles. Vortex rings may be mechanically aimed by positioning vortex ring generator 122 in a desired direction or by deflecting vortex rings upon launch. In some cases, vortex rings may be better aimed after launch using aiming nozzle 129. For example, in one embodiment, aiming nozzle 129 is an air nozzle that uses compressed air to steer a vortex ring toward a target after launch. Aiming nozzle 129 may use bursts of air or a continuous stream to steer or aim a launched vortex ring. In some cases, a launched vortex ring may be driven off course (e.g., by environmental factors) or the intended target may move. In such cases, aiming nozzle 129 may steer the launched vortex ring back on course and toward the intended target. Aiming nozzle 129 typically uses air to steer a vortex ring but may also use other types of gases. Aiming nozzle 129 may be used to create a pressure gradient such that the pressure gradient causes a vortex ring to be sent in a desired direction. Aiming nozzle 129 may also cause vortex rings to spin about a propagation axis. Aiming nozzle 129 may also direct air at a vortex ring to increase the speed of the ring. For example, if the intended target begins to move, aiming nozzle 129 may shoot a stream of air at a launched vortex ring such that the vortex ring reaches the intended target faster and before the intended target moves out of the ring's flight path. In another example, a first vortex ring is launched and then a second vortex ring is launched. An aiming nozzle may shoot a burst of air at the second vortex ring such that the second vortex ring intercepts the first vortex ring. Intercepting a first vortex ring with a second vortex ring may be used to steer or aim the first vortex ring, change the speed of the first vortex ring (e.g., increase the speed if launched from the same direction and decrease the speed if launched from a different or even opposite direction), or combine the two vortex rings creating a larger vortex ring or altering the added components of the first vortex ring.

Referring back to FIG. 1, monitoring module 130 provides data to control module 110 to ensure that vortex rings reach the intended target. Monitoring module 130 may include multiple sensors that monitor or track the intended target, launched vortex rings, and environmental surroundings of vortex ring delivery system 100. In one embodiment, monitoring module 130 includes target sensor 132, vortex ring sensor 134, and environment sensor 136.

Target sensor 132 identifies, monitors, and tracks targets to accurately deliver vortex rings. Target sensor 132 may be or include a motion detector, camera, infrared sensor, microwave sensor, ultrasound, or radar, among others. Target sensor 132 may include multiple sensor types. Target sensor 132 may provide data to control module 110 based on the orientation of the target. For example, in cases where vortex rings are to be delivered to a specific body part of the intended target, the head of the intended target, a specific side of the intended target's nose, or to a particular nostril, target sensor 132 detects the orientation of the target and provides the data to control module 110. In one embodiment, upon receiving data from target sensor 132, control module 110 may determine that added components should only be added to a certain portion of a vortex ring or that added components should be concentrated in a certain portion of a vortex ring. Portions of the rings may also include different gases so that multiple, but distinct, gases are delivered simultaneously. Multiple components may be added to a single vortex ring or a series of vortex rings may each include individual rings of different gases. Vortex rings may be launched to cause the intended target to make a desired reaction, for example, walk in a certain direction or turn their head a certain way. The desired reaction may be to cause the intended target to maintain a desired position or to not move at all. The desired reaction may be to cause the intended target to react, for example, to sneeze, blink, or cough.

Control module 110 may cause a single vortex ring to be delivered or a sequence of vortex rings to be delivered depending on the desired reaction. Target sensor 132 may monitor the intended target's reaction to a first vortex ring, or first series of rings, and provide reaction data to control module 110, which, in turn, determines if additional vortex rings should be delivered based on the reaction data. Upon receiving data from target sensor 132 relating to the intended target's response to a vortex ring, control module 110 may provide an input to vortex ring delivery module 120 to modify the delivery of subsequent vortex rings. For example, after a first vortex ring containing smellable components is received by a target, subsequent vortex rings may have different concentrations of smellable components, subsequent vortex rings may be delivered at higher frequency, or subsequent vortex rings may contain different combinations of smellable components. Control module 110 may use sensor data to time delivery of vortex rings such that the rings arrive at the intended target so as to coincide with a particular event. For example, in one embodiment, target sensor 132 is configured to monitor the breathing patterns of an intended target and provide the data to control module 110, which then launches vortex rings such that the vortex rings reach the intended target when the intended target inhales.

Vortex ring sensor 134 tracks vortex rings launched by vortex ring delivery module 120. Vortex ring sensor 134 may track vortex rings using many different types of sensors, including motion detectors, camera, infrared, microwave, ultrasound, radar, or fluorescence sensors, among others. Vortex ring sensor 134 may include multiple sensor types and may monitor several aspects of a launched vortex ring, for example, the number of vortex rings to reach a target, the direction and speed of a vortex ring, rate of rotation, and added components in the vortex ring, among others. In one embodiment, target sensor 132 monitors a launched vortex ring and provides data relating to the vortex ring to control module 110. Target sensor 132 may provide data to control module 110 such that control module 110 determines if vortex ring delivery module 120 should steer the vortex ring toward the target, launch additional vortex rings, or otherwise alter the launched vortex ring. For example, control module 110 uses data regarding the trajectory of a first vortex ring to aim a second vortex ring. Target sensor 132 may detect characteristics of the target, for example, gender, ethnicity, height, weight, style of clothing. In another example, control module 110 uses data regarding the trajectory of a first series of vortex rings to aim a second series of vortex rings. In some embodiments, fluorescent components that cannot be seen by the human eye are added to vortex rings such that the fluorescent components may be detected by a fluorescent sensor. Other fluorescent components may be added that may be seen by humans or that are excitable by ambient illumination or tracking illumination (e.g., emitted by an illumination source in monitoring module 130). Fluorescent components may be added to each vortex ring of a sequence, or to only a subset of vortex ring (e.g., every 5th vortex ring).

Environment sensor 136 monitors the environment surrounding vortex ring delivery system 100. Environment sensor 136 may track air flow, wind, temperature, humidity, pressure gradients, and magnetic fields, among others. Environment sensor 136 may include multiple sensor types. In one embodiment, environment sensor 136 monitors the environmental surroundings of vortex ring delivery system 100 and provides data to control module 110. Control module 110 uses data provided by environment sensor 136 to ensure vortex rings reach the intended target. For example, in one embodiment, upon detecting and measuring a pressure gradient that will affect the travel of vortex rings, environment sensor 136 provides data to control module 110, which in turn determines how vortex ring delivery module 120 should launch and steer a vortex ring such that the vortex ring reaches the intended target. In some cases, vortex ring delivery module 120 relies on the surrounding environment to deliver vortex rings. For example, control module 110 may determine, based on inputs from environmental sensor 136 and target sensor 132, that local airflow is blowing directly at an intended target such that a vortex ring launched from vortex ring delivery module 120 will reach the intended target without further aiming or steering by system 100.

Figure 3:
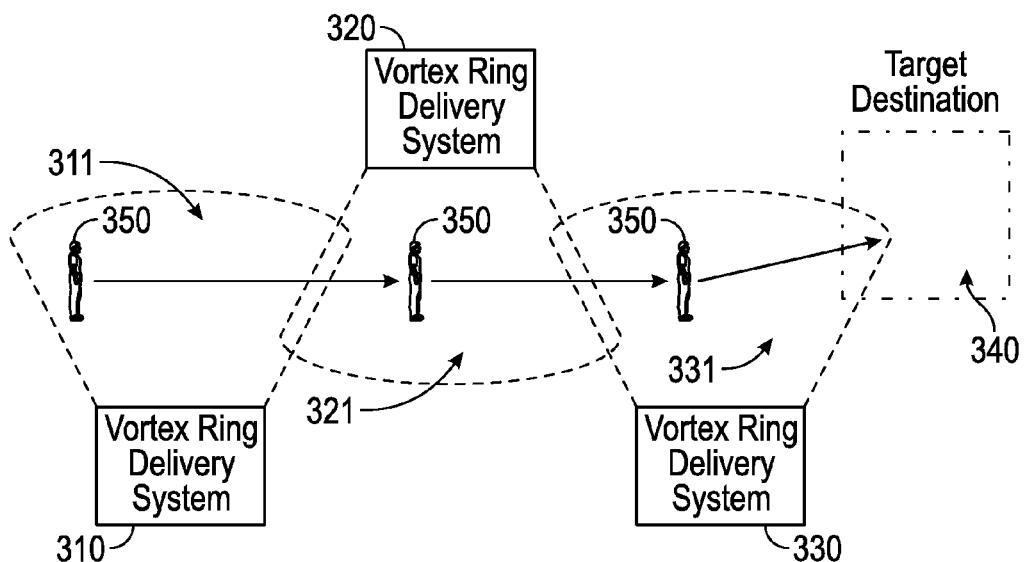

Referring now to FIG. 3, multiple vortex ring delivery systems 100 may be networked together. Vortex ring delivery systems 100 may communicate with one another and work together over large distances. In some cases, multiple vortex ring delivery systems may work together to direct a certain person to a target destination across a large distance. For example, one embodiment includes vortex ring delivery system 310 having range 311, vortex ring delivery system 320 having range 321, and vortex ring delivery system 330 having range 331. Upon vortex ring delivery system 310 identifying intended target 350, system 310 delivers vortex rings such that intended target 350 walks out of range 311 and into range 321. Upon entering range 321, vortex ring delivery system 320 detects intended target 350 and delivers vortex rings such that intended target 350 walks out of range 321 and into range 331. Upon entering range 331, vortex ring delivery system 330 detects intended target 350 and delivers vortex rings such that intended target 350 walks out of range 331 and into target destination 340.

Vortex ring delivery systems may communicate and share data with other vortex ring delivery systems by cable media or wireless media. When networked together, vortex ring delivery systems can work together to reach a common goal. For example, as shown in FIG. 3, vortex ring delivery systems 310, 320, 330 work together to lead intended target 350 to target destination 340. After identifying intended target 350 and target destination 340, system 310 determines that target destination 340 is outside of range 311 and that intended target 350 must be led to closer systems in order to successfully lead intended target 350 to target destination 340. Vortex ring delivery systems may also share information relating to intended targets, including identification information, previous vortex ring deliveries to an intended target, an intended target's previous reactions to certain added components, etc. In one embodiment, vortex ring delivery systems are linked to a common database containing accumulated targeting information, reaction data, and other data regarding vortex ring delivery.

Figure 4:
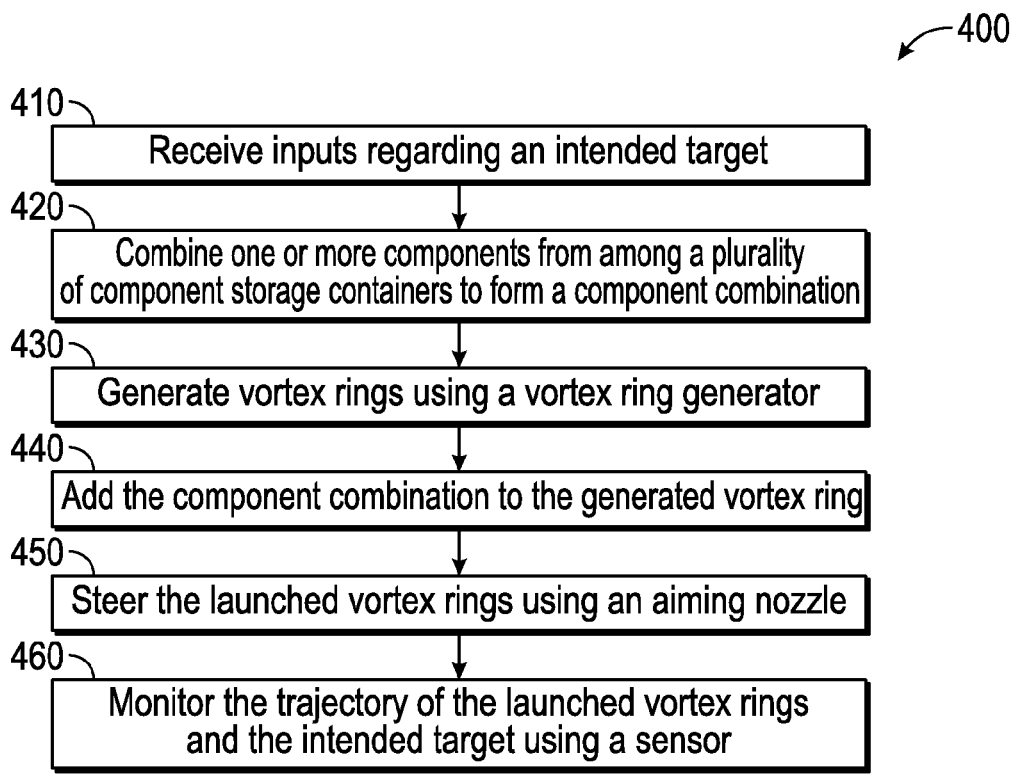

Referring now to FIG. 4, method 400 for delivering vortex rings is shown according to one embodiment. According to one embodiment, method 400 is a computer-implemented method utilizing system 100. Method 400 may be implemented using any combination of computer hardware and software. According to one embodiment, inputs regarding intended targets are received (410). For example, control module 110 may receive a user input to target young adults. Next, one or more components are combined from among a plurality of component storage containers to form a component combination (420). For example, control module 110 may choose a food-enhancing component contained in component storage container 124. Next, vortex rings are generated using vortex ring generator 122 (430). For example, vortex rings may be generated using the assembly shown in FIG. 2 including nozzle 210 and hollow cylinder 230. Next, the component combination is added to the generated vortex rings (440). For example, component additive mechanism 128 may add components by nozzle 128 or mesh 229. Next, the generated vortex rings are steered using an aiming nozzle (450). For example, after launching vortex rings, aiming nozzle 129 may shoot bursts of air at the launched rings to steer the rings toward the intended target. Next, the trajectory of the launched vortex rings are monitored and the intended target is monitored using a sensor (e.g., monitoring module 130) (460).

Figure 5:
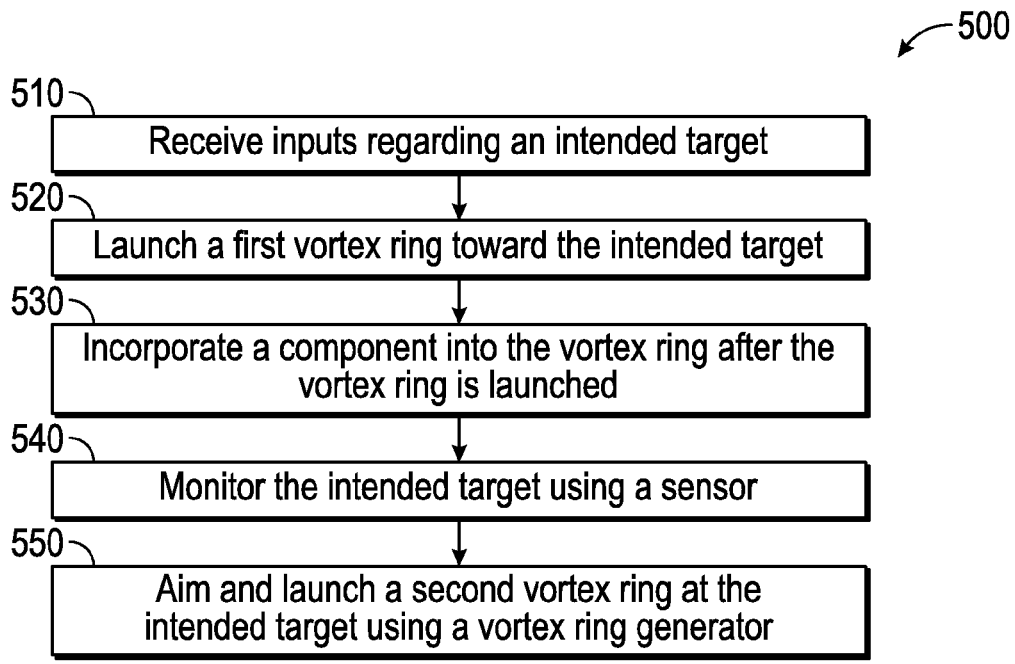

Referring next to FIG. 5, method 500 for delivering vortex rings is shown according to one embodiment. According to one embodiment, method 500 is a computer-implemented method utilizing system 100. Method 500 may be implemented using any combination of computer hardware and software. According to one embodiment, inputs regarding an intended target are received (510). For example, control module 110 may receive a user input to target seniors. Next, a first vortex ring is launched toward the intended target (520). For example, vortex rings may be launched using the assembly shown in FIG. 2 including nozzle 210 and hollow cylinder 230. Next, a component is incorporated into the first vortex ring after the vortex ring is launched (e.g., by vortex ring generator 122) (530). For example, component additive mechanism 128 may add components by nozzle 128 or mesh 229. Next, the intended target is monitored using a sensor (e.g., target sensor 132) (540). Finally, a second vortex ring is aimed and launched at the intended target using vortex ring generator 122 (550).

Figure 6:
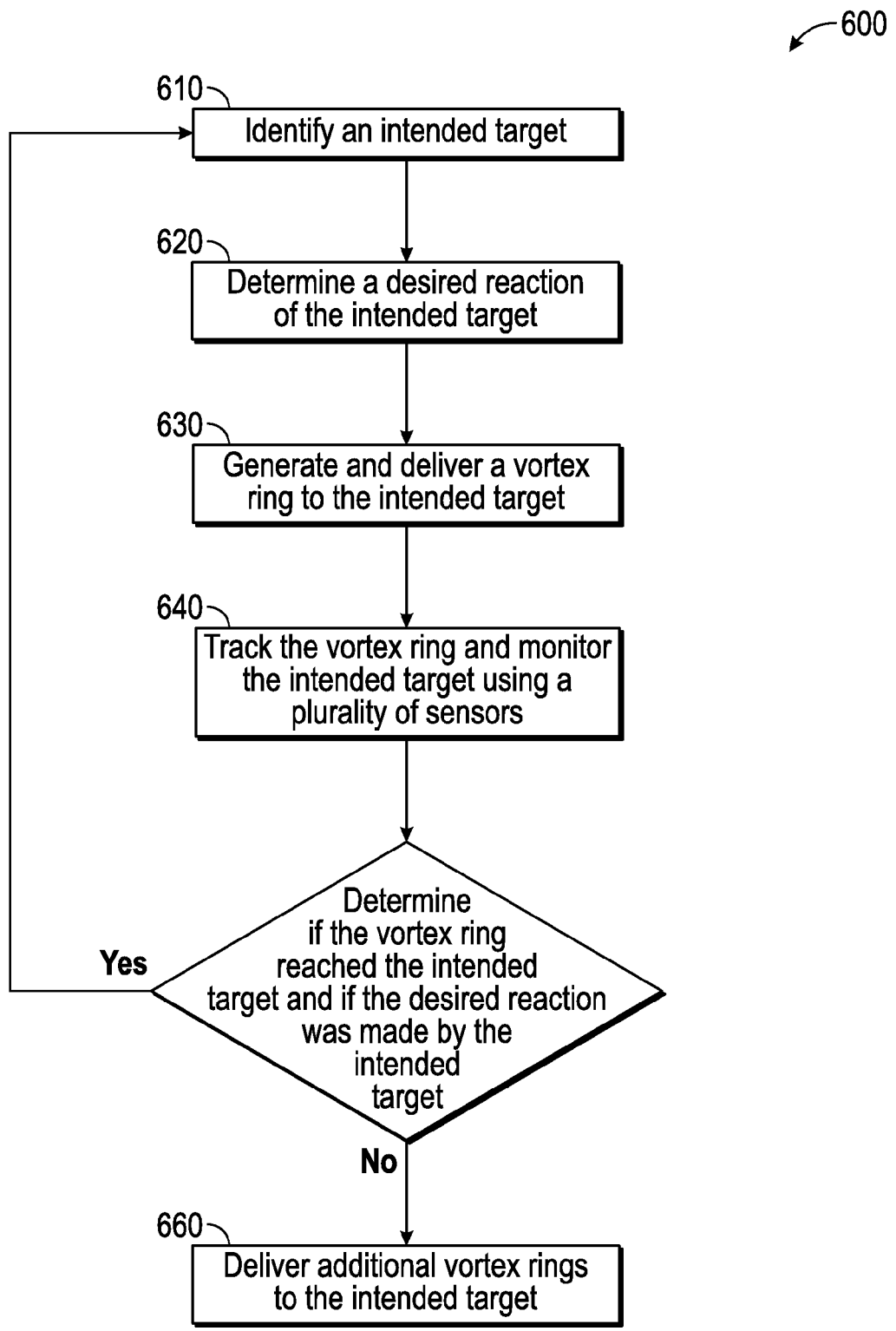

Referring next to FIG. 6, method 600 for delivering vortex rings is shown according to one embodiment. According to one embodiment, method 600 is a computer-implemented method utilizing system 100. Method 600 may be implemented using any combination of computer hardware and software. According to one embodiment, an intended target is identified (610). For example, control module 110 may receive a user input to target young adults. Next, a desired reaction of the intended target is determined, for example, by control module 110 (620). For example, control module 110 may determine that the intended target should enter or remain in a department store. Next, a vortex ring is generated and delivered to the intended target, for example, by vortex ring generator 120 (630). For example, vortex rings may be generated using the assembly shown in FIG. 2 including nozzle 210 and hollow cylinder 230. The vortex ring is tracked and the intended target is monitored (e.g., by monitoring module 130) using a plurality of sensors (e.g., target sensor 132 and vortex ring sensor 134) (640). Next, a determination is made (e.g., by control module 110) if the vortex ring reached the intended target and if the desired reaction was made by the intended target, and whether additional vortex rings should be delivered (650). Finally, if control module 110 determines the intended target did not make the desired reaction, then additional vortex rings are delivered to the intended target (660), otherwise, a new target is identified (610).

Vortex ring delivery system 100 may be configured to deliver vortex rings for a variety of purposes and under many different scenarios. For example, vortex ring delivery may be timed so as to coincide with a particular event (e.g., the intended target inhaling); multiple smells may be delivered simultaneously (e.g., different portions of a ring may have different smells or include a scent gradient) or in desired sequence; added smellable components may be generic or selected for the specific target (e.g., selected based on gender, age, height, style of clothing, ethnicity, etc.); scents may be vaporized with ultrasound; scents may cling to clothing to have a longer affect which may be reinforced with scent reminders and targeted marketing while the intended target moves about; gas delivery may be used for games, advertising, memory lock-in/reinforcement; launched vortex rings may be spun about a propagation axis; and launched vortex rings may be imbedded with florescent molecules such that the rings may be seen when a light is shone on the rings.

The present disclosure contemplates methods, systems, and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for delivering vortex rings, comprising:
receiving, by a control module, inputs regarding an intended target;
combining one or more components to form a gas combination;
generating vortex rings using a vortex ring generator;
adding, by a component additive mechanism, the gas combination to the generated vortex rings;
steering the generated vortex rings using an aiming nozzle; and
monitoring the trajectory of the launched vortex rings and the intended target using a sensor.

2. The method of claim 1, further comprising aiming vortex rings using an aiming nozzle based on sensor data acquired by the sensor.

3. The method of claim 2, further comprising controlling operation of the aiming nozzle to direct a first vortex ring based on the sensor data, wherein the sensor data includes data regarding the trajectory of the first vortex ring.

4. The method of claim 2, further comprising controlling operation of the aiming nozzle to direct a second vortex ring based on the sensor data, wherein the sensor data includes data regarding the trajectory of a first vortex ring.

5. The method of claim 2, further comprising controlling operation of the aiming nozzle to direct a second series of vortex rings based on the sensor data, wherein the sensor data includes data regarding the trajectory of a first series of vortex rings.

6. The method of claim 1, wherein the vortex rings include a fluorescent component.

7. The method of claim 6, wherein the fluorescent component is at least one of visible, non-visible, excitable by ambient illumination, or excitable by dedicated tracking illumination.

8. The method of claim 1, wherein a first vortex ring is intercepted and modified by a second vortex ring.

9. The method of claim 8, wherein the second vortex ring steers the first vortex ring.

10. The method of claim 8, wherein the second vortex ring causes the speed of the first vortex ring to change.

11. The method of claim 1, wherein the vortex rings are aimed to be delivered to a specific body part of the intended target.

12. The method of claim 1, wherein vortex rings are launched in a sequence to cause the intended target to make a desired reaction.

13. The method of claim 12, wherein the desired reaction is to lead the intended target in a desired direction.

14. The method of claim 1, wherein the delivery of subsequent vortex rings is modified based on the response of the intended target to a first vortex ring.

15. The method of claim 14, wherein the modification comprises changing the aiming of the subsequent vortex rings.

16. A method for delivering vortex rings, comprising:
    receiving inputs regarding an intended target using a control module;
    launching a first vortex ring toward the intended target using a vortex ring generator;
    incorporating a gas into the first vortex ring using a component additive mechanism;
    acquiring sensor data regarding the intended target using a sensor; and
    aiming and launching a second vortex ring at the intended target using the vortex ring generator based on the sensor data;
    wherein the component additive mechanism includes a mesh containing one or more components, and wherein the vortex rings travel through the mesh before the vortex rings reach the intended target.

17. The method of claim 16, wherein the component comprises at least one of a fluorescent component, a smellable component, a smell-canceling component, a medicinal component, and a hormonal component.

18. The method of claim 16, further comprising adding smellable components to the vortex rings before the vortex rings are launched.

19. The method of claim 16, wherein the component additive mechanism is configured to add one or more components to the vortex rings before or during the generation of the vortex rings.

20. The method of claim 16, further comprising adding multiple components to the vortex rings using the component additive mechanism.

21. The method of claim 16, further comprising controlling adding smellable components to the vortex rings before the vortex rings reach the intended target using the component additive mechanism.

22. The method of claim 21, wherein the smellable components are pheromones.

23. The method of claim 16, wherein a first vortex ring is intercepted and modified by a second vortex ring.

24. The method of claim 23, wherein the second vortex ring steers the first vortex ring.

25. The method of claim 23, wherein the second vortex ring causes the speed of the first vortex ring to change.

26. A method for delivering directional smell cues, comprising:
    identifying an intended target;
    determining a desired reaction of the intended target;
    generating and delivering vortex rings to the intended target using a vortex ring generator and component additive mechanism;
    tracking the vortex rings and monitoring the intended target using a sensor; and
    selectively delivering additional vortex rings based on determining if the vortex ring reached the intended target and if the desired reaction was made by the intended target;
    wherein the component additive mechanism includes a mesh containing one or more components, and wherein the vortex rings travel through the mesh before the vortex rings reach the intended target.

27. The method of claim 26, further comprising aiming the vortex rings based on data provided by a sensor.

28. The method of claim 27, wherein the sensor monitors the trajectory of the vortex ring being aimed.

29. The method of claim 27, further comprising aiming a second vortex ring based on data provided by the sensor, wherein the data provided by the sensor includes trajectory data of a first vortex ring.

30. The method of claim 26, wherein the vortex rings include a fluorescent component.

31. The method of claim 30, wherein the fluorescent component is at least one of visible, non-visible, excitable by ambient illumination, or excitable by dedicated tracking illumination.

32. The method of claim 26, further comprising controlling adding one or more components to the vortex rings using the component additive mechanism before or during the generation of the vortex rings.

33. The method of claim 26, further comprising controlling adding multiple components to the vortex rings using the component additive mechanism.

\* \* \* \* \*